(12) United States Patent
Shintani et al.

(10) Patent No.: US 9,373,506 B2
(45) Date of Patent: Jun. 21, 2016

(54) METHOD FOR TREATING SURFACE OF DIAMOND THIN FILM, METHOD FOR FORMING TRANSISTOR, AND SENSOR DEVICE

(71) Applicants: YOKOGAWA ELECTRIC CORPORATION, Musashino-shi, Tokyo (JP); WASEDA UNIVERSITY, Shinjuku-ku, Tokyo (JP)

(72) Inventors: Yukihiro Shintani, Musashino (JP); Toshiyuki Saruya, Musashino (JP); Hiroshi Kawarada, Shinjuku-ku (JP)

(73) Assignees: YOKOGAWA ELECTRIC CORPORATION, Tokyo (JP); WASEDA UNIVERSITY, Tokyo (JP)

( * ) Notice: Subject to any disclaimer, the term of this patent is extended or adjusted under 35 U.S.C. 154(b) by 0 days.

(21) Appl. No.: 14/467,153

(22) Filed: Aug. 25, 2014

(65) Prior Publication Data

US 2015/0054000 A1 Feb. 26, 2015

(30) Foreign Application Priority Data

Aug. 26, 2013 (JP) .................. 2013-175059
Jul. 4, 2014 (JP) .................. 2014-138972

(51) Int. Cl.
| | | |
|---|---|---|
| H01L 29/15 | (2006.01) | |
| H01L 21/04 | (2006.01) | |
| C23C 16/27 | (2006.01) | |

(Continued)

(52) U.S. Cl.
CPC .............. *H01L 21/042* (2013.01); *C23C 16/27* (2013.01); *C23C 16/56* (2013.01); *G01N 27/4145* (2013.01); *H01L 21/3065* (2013.01); *H01L 29/66045* (2013.01)

(58) Field of Classification Search
CPC ........................... H01L 21/3065; H01L 21/042
USPC .......................................................... 257/77
See application file for complete search history.

(56) References Cited

U.S. PATENT DOCUMENTS

| | | | |
|---|---|---|---|
| 5,665,435 A | | 9/1997 | Smentkowski et al. |
| 6,136,722 A | | 10/2000 | Nambu |

(Continued)

FOREIGN PATENT DOCUMENTS

| | | |
|---|---|---|
| JP | 10-125672 A | 5/1998 |
| JP | 11-121438 A | 4/1999 |

(Continued)

OTHER PUBLICATIONS

Schvartzman et al., "Plasma fluorination of diamond-like carbon surfaces: mechanism and application to nanoimprint lithography," Nanotechnology, IOP, Apr. 8, 2009, vol. 20, No. 14, pp. 1-7 (7 pages total).

*Primary Examiner* — Douglas Menz
(74) *Attorney, Agent, or Firm* — Sughrue Mion, PLLC

(57) ABSTRACT

A method for treating a surface of a diamond thin film according to one aspect of the present invention performs one of a first substitution process for substituting part of hydrogen-terminals of a diamond thin film with fluorine-terminals in the absence of a fluorocarbon deposition on the surface of diamond thin film and a second substitution process for substituting part of hydrogen-terminals of a diamond thin film with fluorine-terminals in the presence of the fluorocarbon deposition on the surface of diamond thin film based on required surface properties of the diamond thin film.

17 Claims, 13 Drawing Sheets

(51) Int. Cl.
*C23C 16/56* (2006.01)
*G01N 27/414* (2006.01)
*H01L 21/3065* (2006.01)
*H01L 29/66* (2006.01)

(56) References Cited

U.S. PATENT DOCUMENTS

2010/0084634 A1 4/2010 Gamo
2012/0199884 A1* 8/2012 Shintani et al. ............... 257/253

FOREIGN PATENT DOCUMENTS

| | | |
|---|---|---|
| JP | 2006-097054 A | 4/2006 |
| JP | 3886922 B2 | 2/2007 |
| JP | 2007-253410 A | 10/2007 |
| JP | 2007-253544 A | 10/2007 |
| JP | 4119973 B2 | 7/2008 |
| JP | 2011-029372 A | 2/2011 |
| JP | 2012-168120 A | 9/2012 |
| WO | 2005/116306 A1 | 12/2005 |

* cited by examiner

METHOD FOR TREATING SURFACE OF DIAMOND THIN FILM, METHOD FOR FORMING TRANSISTOR, AND SENSOR DEVICE

BACKGROUND OF THE INVENTION

1. Field of the Invention

The present invention relates to a method for treating a surface of diamond thin film, a method for forming a transistor, and a sensor device.

Priority is claimed on Japanese Patent Application No. 2013-175059, filed Aug. 26, 2013 and Japanese Patent Application No. 2014-138972, filed Jul. 4, 2014, the contents of which are incorporated herein by reference.

2. Description of Related Art

Research and development of sensor devices for detecting a specific material included in a solution (an electrolyte solution), such as ion sensors for detecting an ion concentration in a solution, and biosensors for detecting organic materials including protein materials, glucose, and the like in a solution, has been actively performed. One of the sensor devices includes a field-effect transistor where a source electrode and a drain electrode are formed on a diamond thin film and the surface of diamond thin film positioned between the source electrode and the drain electrode, with which the solution is in contact, acts as a gate. Since the field-effect transistor includes the diamond thin film being in contact with the solution, the field-effect transistor has the advantages that the stability is high, the forming is easy, and the cost is low.

Japanese Unexamined Patent Application, First Publication No. 2012-168120 (referred to as PTL 1) discloses an ion sensor including the field-effect transistor described above. Specifically, PTL1 discloses an ion sensor including a reference electrode and a working electrode. A detection target solution is held between the reference electrode and the working electrode, and each of the reference electrode and the working electrode are configured by the field-effect transistor described above (a p-channel field-effect transistor). Additionally, PTL 1 discloses that the ion sensitivity is controlled by performing a hydrogen-termination with respect to the surface of diamond thin film functioning as a gate, and then, performing an oxygen-termination or a fluorine-termination with respect to a part of the surface of a diamond thin film.

Japanese Unexamined Patent Application, First Publication No. 2006-97054 (referred to as PTL 2), Japanese Patent No. 3886922 (referred to as PTL 3), and Japanese Patent No. 4119973 (referred to as PTL 4) disclose techniques for treating a surface of diamond (a fluorine treatment). Specifically, PTL 2 discloses that the life prolongation is achieved by performing a fluorination treatment (a thermal fluorine treatment, an electrolytic fluorine treatment) with respect to a conductive substrate covered with a conductive diamond. PTL 3 discloses that a density of hole is increased by exposing a surface of diamond to plasma including a mixed gas of hydrogen and fluorine sulfide to treat a surface of a diamond substrate. PLT4 discloses that a fluorine functional group is easily introduced by irradiating a solution including a diamond powder and perfluoroazoalkane with ultraviolet to chemically connect the surface of diamond powder with perfluoroazoalkyl group.

As disclosed in PTL1, it is thought that the ion sensitivity of field-effect transistor can be changed at will by terminating a part of the hydrogen-terminated diamond surface with fluorine. However, by studies of the inventors of the present application, when a fluorine treatment is performed with respect to a surface of diamond, it has come to be understood that a fluorocarbon deposited film is formed depending on the processing method.

As is well known, a fluorocarbon is a collective term of an organic compound including carbon-fluorine bond (C—F), and has a property that a chemical reaction tends not to occur and it is stable if the temperature is changed. Therefore, when a part of the hydrogen terminated diamond surface is fluorine terminated, if such a fluorocarbon deposited film is formed on the diamond surface, there are some cases where the property (nature) of the diamond surface becomes different from a primary intended property. Thereby, the ion sensitivity of the field-effect transistor becomes different from a primary intended ion sensitivity, then, there are some cases where sensor devices including a property different from a primary one are formed.

Therefore, in order to form sensor devices including intended properties, it is quite important to control the presence or absence of the deposited film of fluorocarbon when the diamond surface, which acts as a gate of field-effect transistor, is processed. PTLs 2 to 4 described above disclose a technique for treating a diamond surface (a fluorine treatment), but do not mention that the fluorocarbon deposited film is formed when the diamond surface is treated.

SUMMARY OF THE INVENTION

One aspect of the present invention provides a method for treating a surface of diamond thin film capable of making the diamond surface have a desired property by controlling the presence or absence of a fluorocarbon deposited film, a method for forming a transistor using the surface treating method, and a sensor device including a transistor formed by the forming method.

A method for treating a surface of a diamond thin film according to one aspect of the present invention may include performing, based on required surface properties of the diamond thin film, one of: a) a first substitution process for substituting part of hydrogen-terminals of the diamond thin film with fluorine-terminals in the absence of a fluorocarbon deposition on the surface of the diamond thin film; and b) a second substitution process for substituting part of hydrogen-terminals of the diamond thin film with fluorine-terminals in the presence of the fluorocarbon deposition on the surface of the diamond thin film.

In the method for treating the surface of the diamond thin film described above, the method may further include substituting any terminals other than hydrogen terminals of the surface of the diamond thin film with hydrogen terminals, prior to performing the one of the first and second substitution processes.

In the method for treating the surface of the diamond thin film described above, the first substitution process may be to expose at least a part of the surface of the diamond thin film to a fluorine gas or a fluorine-based gas.

In the method for treating the surface of the diamond thin film described above, the first substitution process may to perform a reactive ion etching exposing at least a part of the surface of the diamond thin film to a fluorine-based gas.

In the method for treating the surface of the diamond thin film described above, the reactive ion etching may include an inductive coupled reactive ion etching.

In the method for treating the surface of the diamond thin film described above, the second substitution process may be to perform a reactive ion etching exposing at least a part of the surface of the diamond thin film to a fluorine-based gas.

In the method for treating the surface of the diamond thin film described above, the reactive ion etching may include an inductive coupled reactive ion etching.

In the method for treating the surface of the diamond thin film described above, the fluorine-based gas used for exposure in the first substitution process may include $XeF_2$ or $COF_2$.

In the method for treating the surface of the diamond thin film described above, the fluorine-based gas used for the reactive ion etching in the first substitution process may include at least one of $C_xF_y$, $C_xH_yF_z$, $S_xF_y$, $N_xF_y$, $C_xO_yF_z$, $N_xO_yF_z$, and $S_xO_yF_z$, where each x, y, and z is the integer equal to or greater than 1.

In the method for treating the surface of the diamond thin film described above, the fluorine based gas used for the reactive ion etching in the second substitution process may include at least one of $C_xF_y$, $C_xH_yF_z$, $S_xF_y$, $N_xF_y$, $C_xO_yF_z$, $N_xO_yF_z$, and $S_xO_yF_z$, where each x, y, and z is integer equal to or greater than 1.

In the method for treating the surface of the diamond thin film described above, the first and second substitution processes may be to perform an inductive coupled reactive ion etching exposing at least a part of the surface of the diamond thin film to a fluorine-based gas. One of the first and second substitution processes may be performed by controlling the power source output and the process time of the inductive coupled reactive ion etching.

A method for forming a transistor according to one aspect of the present invention may include forming a diamond thin film, performing the method for treating the surface of the diamond thin film described above with substituting part of hydrogen-terminals on at least an area of the surface of the diamond thin film, and forming a gate on the area of the surface of the diamond thin film.

In the method for forming the transistor described above, the method may further include forming a source electrode and a drain electrode on the diamond thin film after forming the diamond thin film and before performing the surface treatment.

In the method for forming the transistor described above, forming the source electrode and the drain electrode may include forming a protection film for protecting the source electrode and the drain electrode to cover the source electrode and the drain electrode.

In the method for forming the transistor described above, performing the surface treatment may include substituting any terminals other than hydrogen terminals of the surface of the diamond thin film with hydrogen terminals, prior to performing the one of the first and second substitution processes.

In the method for forming the transistor described above, the first substitution process may be to expose at least a part of the surface of the diamond thin film to a fluorine gas or a fluorine-based gas.

In the method for forming the transistor described above, the first substitution process may to perform a reactive ion etching exposing at least a part of the surface of the diamond thin film to a fluorine-based gas.

In the method for forming the transistor described above, the second substitution process may be to perform a reactive ion etching exposing at least a part of the surface of the diamond thin film to a fluorine-based gas.

In the method for forming the transistor described above, the first and second substitution processes may be to perform an inductive coupled reactive ion etching exposing at least a part of the surface of the diamond thin film to a fluorine-based gas. One of the first and second substitution processes may be performed by controlling the power source output and the process time of the inductive coupled reactive ion etching.

A sensor device according to one aspect of the present invention may include at least one detection electrode configured to contact with a liquid including a specific material. The sensor device may be for detecting the specific material included in the liquid based on output from the detection electrode. A transistor formed by the method for forming a transistor according described above may be provided in the detection electrode so as to bring the surface of the diamond thin film acting as the gate with the liquid.

According to one aspect of the present invention, one of a first substitution process for substituting part of hydrogen-terminals of a diamond thin film with fluorine-terminals in the absence of a fluorocarbon deposition on a surface of diamond thin film and a second substitution process for substituting part of hydrogen-terminals of a diamond thin film with fluorine-terminals in the presence of the fluorocarbon deposition on a surface of diamond thin film. Thereby, one aspect of the present invention includes effects of making the diamond surface have a desired property.

DETAILED DESCRIPTION OF THE INVENTION

Hereinafter, a method for treating a surface of diamond thin film, a method for forming a field-effect transistor, and a sensor device according to an embodiment of the present invention will be described in detail, with references made to the drawings. Hereinafter, an example that a sensor device is a pH sensor will be described. In addition, regarding the method for treating the surface of diamond thin film and the method for forming the field-effect transistor, an example that a field-effect transistor provided in a sensor device is formed will be described.

(First Embodiment)
<Sensor Device>

Figure 1:
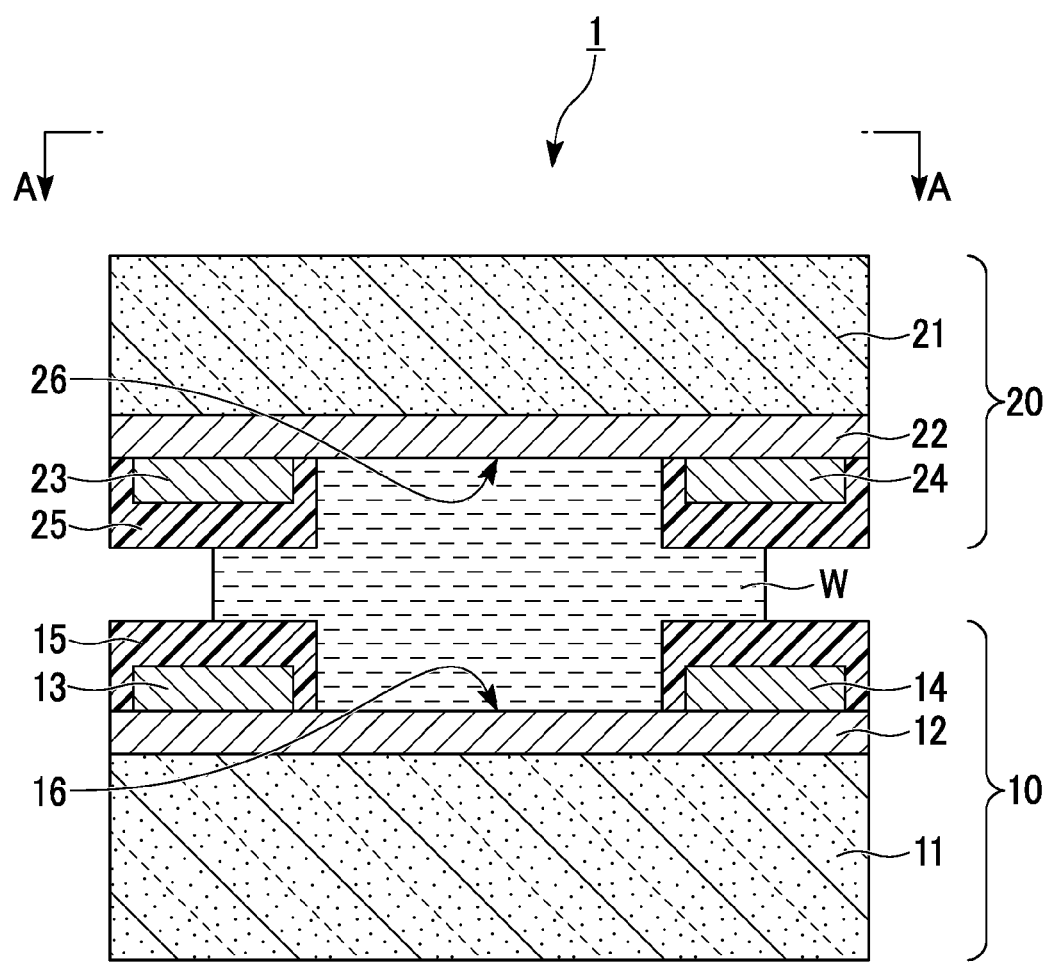
FIG. 1 is a cross-section diagram showing a configuration of a pH sensor as a sensor device according to a first embodiment of the present invention.
Figure 2:
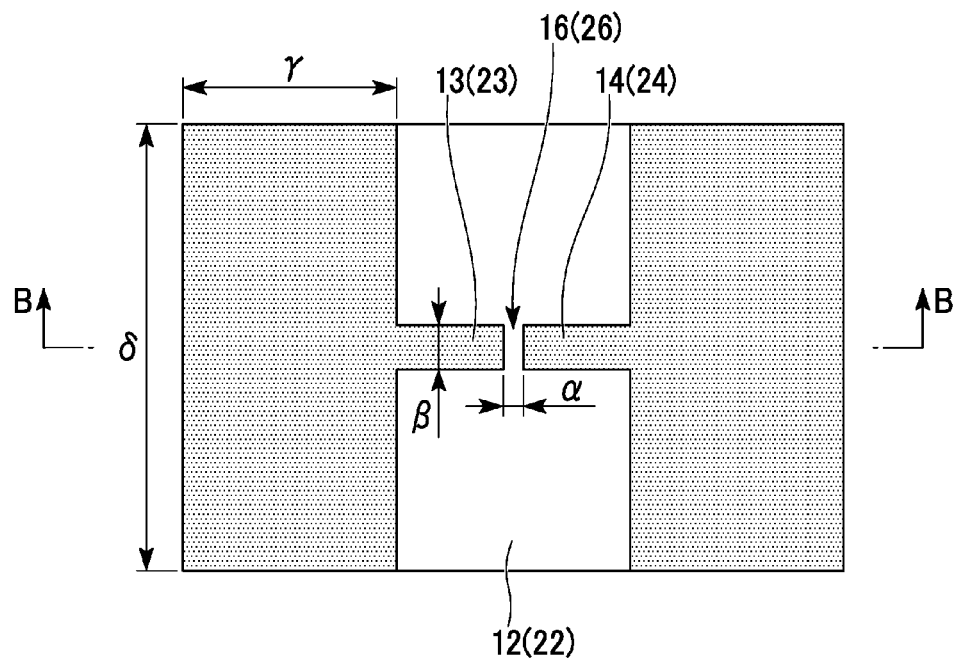
FIG. 2 is a plan perspective diagram of the pH sensor as a sensor device according to the first embodiment of the present invention.

FIG. 1 is a cross-section diagram showing a configuration of a pH sensor as a sensor device according to a first embodiment of the present invention. FIG. 2 is a plan perspective diagram of the pH sensor. FIG. 1 is a cross-section arrow diagram along B-B line in FIG. 2, and FIG. 2 is a plan perspective diagram viewing the pH sensor from A-A direction in FIG. 1. As shown in FIGS. 1 and 2, the pH sensor 1 includes a reference electrode 10 (a detection electrode) and a working electrode 20 (a detection electrode). The reference electrode 10 is opposed to the working electrode 20. The pH of a measured liquid W (solution) guided to between the reference electrode 10 and the working electrode 20 is measured.

The reference electrode 10 includes a silicon wafer 11 (substrate), a diamond thin film 12, a source electrode 13, a drain electrode 14, and a protection film 15. The diamond thin film 12 is formed on the surface of silicon wafer 11, and the source electrode 13 and the drain electrode 14 are formed on the surface of diamond thin film 12 so as to be opposite to each other. The protection film 15 is formed on the diamond thin film 12 to cover the source electrode 13 and the drain electrode 14. In this reference electrode 10, the area between the source electrode 13 and the drain electrode 14 (the surface of diamond thin film 12) acts as a gate 16.

A p-channel field-effect transistor including the source electrode 13, the drain electrode 14, and the gate 16 is formed in the reference electrode 10. Since a measured liquid W is guided to the gate 16 of the p-channel field-effect transistor, it may be referred to as an ion-sensitive field-effect transistor (ISFET). Since the ion-sensitive field-effect transistor includes the diamond thin film 12, it may also be referred to as a diamond ISFET. Since the ion-sensitive field-effect transistor includes the diamond thin film 12 and does not have an oxide at a liquid contact part of diamond, it may also be referred to as a diamond SGFET (electrolyte Solution-Gate FET).

The size of the gate 16 is appropriately set based on the property of pH sensor. For example, as shown in FIG. 2, a gate length $\alpha$ is set to be approximately from 10 μm to 1000 μm, and a gate width $\beta$ is set to be approximately from 0.01 mm to 50 mm. A length $\gamma$ of source electrode 13 (drain electrode 14) is set to be approximately from 0.01 mm to 50 mm, and a width $\delta$ of source electrode 13 (drain electrode 14) is set to be approximately from 0.01 mm to 100 mm.

Elements of the surface terminal of the diamond thin film 12, which acts as the gate 16, are controlled so that the electrical potential is stable when the hydrogen ion concentration is in the range from $1.0 \times 10^{-1}$ to $1.0 \times 10^{-14}$ mol/L, or the electrical potential is maintained constant without substantially causing problems of ion sensitivity. Namely, the surface of diamond thin film 12, which acts as the gate 16, is set to be an ion-insensitive terminal. The details of the surface treatment of diamond thin film 12 will be described later.

The working electrode 20 includes the same configuration as that of the reference electrode 10, and includes a silicon wafer 21 (substrate), a diamond thin film 22, a source electrode 23, a drain electrode 24, and a protection film 25. The diamond thin film 22 is formed on the surface of silicon wafer 21, and the source electrode 23 and the drain electrode 24 are formed on the surface of the diamond thin film 22 so as to be opposite to each other. The protection film 25 is formed on the diamond thin film 22 to cover the source electrode 23 and the drain electrode 24. In this working electrode 20, the area between the source electrode 23 and the drain electrode 24 (the surface of diamond thin film 22) acts as a gate 26.

A p-channel field-effect transistor including the source electrode 23, the drain electrode 24, and the gate 26 is formed in the working electrode 20. Since the measured liquid W is guided to the gate 26 of the p-channel field-effect transistor, it may be referred to as an ion-sensitive field-effect transistor (ISFET).

As shown in FIG. 2, it is preferable to make the source electrode 23 and the drain electrode 24 have the same shape as those of the source electrode 13 and the drain electrode 14 provided in the reference electrode 10, respectively. The sizes of the source electrode 23 and the drain electrode 24 may be different from those of the source electrode 13 and the drain electrode 14 provided in the reference electrode 10, respectively. The interval between the source electrode 23 and the drain electrode 24 may be different from that between the source electrode 13 and the drain electrode 14 provided in the reference electrode 10. It is preferable to set a gate length α, a gate width β, a length γ of the source electrode 23 (drain electrode 24), and a width δ of the source electrode 23 (drain electrode 24) in the ranges of those of the reference electrode 10.

Elements of the surface terminal of the diamond thin film 22, which acts as the gate 26, are controlled so that the electrical potential linearly- or non-linearly-changes based on the pH value when the hydrogen ion concentration is in the range from $1.0 \times 10^{-1}$ to $1.0 \times 10^{-14}$ mol/L. Namely, the surface of the diamond thin film 22, which acts as the gate 26, is set to be an ion-sensitive terminal. The details of the surface treatment of the diamond thin film 22 will be described later.

Next, operations of the pH sensor 1 in the configuration described above will be described below. As shown in FIG. 1, in the reference electrode 10, the area (the surface of diamond thin film 12) between the source electrode 13 and the drain electrode 14, which acts as the gate 16, is in contact with the measured liquid W. On the other hand, since the source electrode 13 and the drain electrode 14 are covered with the protection film 15, the source electrode 13 and the drain electrode 14 are not in contact with the measured liquid W. In the working electrode 20, the area (the surface of diamond thin film 22) between the source electrode 23 and the drain electrode 24, which acts as the gate 26, is in contact with the measured liquid W. On the other hand, since the source electrode 23 and the drain electrode 24 are covered with the protection film 25, the source electrode 23 and the drain electrode 24 are not in contact with the measured liquid W.

Figure 3:
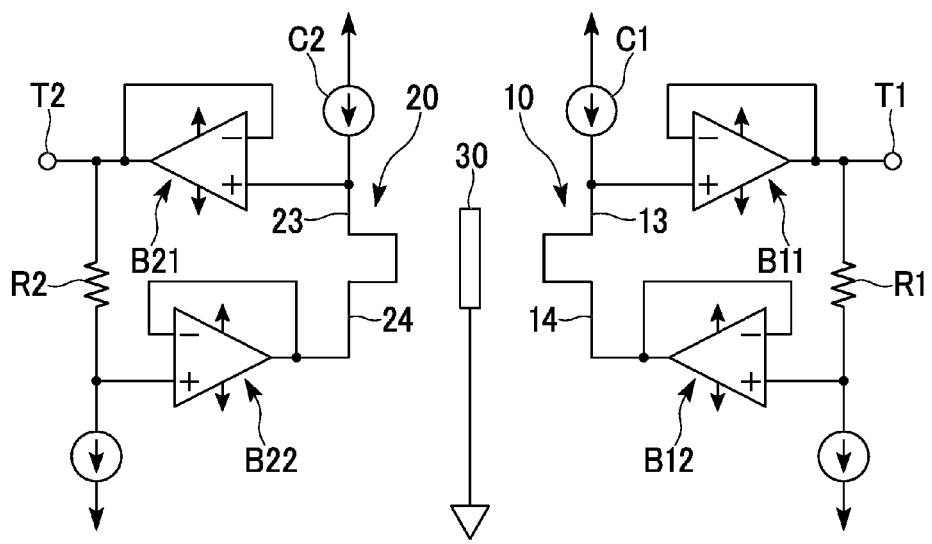
FIG. 3 is a circuit diagram showing an example of a pH measuring circuit using the pH sensor as a sensor device according to the first embodiment of the present invention.

Electric charges in the measured liquid W affect the interfacial potential of the gate 16 and the gate 26, and the results are derived from output terminals T1 and T2 (refer to FIG. 3).

FIG. 3 is a circuit diagram showing an example of pH measuring circuit using the pH sensor as a sensor device according to the first embodiment of the present invention. As shown in FIG. 3, a pseudo-reference electrode 30, which is in contact with the measured liquid W (not shown in FIG. 3), is grounded.

The source electrode 13 of the reference electrode 10 is in contact with a constant current source C1 and a buffer circuit B11, and the drain electrode 14 of the reference electrode 10 is in contact with a buffer circuit B12. The output terminal T1 is in contact with the source electrode 13 of the reference electrode 10 via the buffer circuit B11, and is in contact with the drain electrode 14 of the reference electrode 10 via a resistance R1 and the buffer circuit B12. The source electrode 23 of the working electrode 20 is in contact with a constant current source C2 and a buffer circuit B21, and the drain electrode 24 of the working electrode 20 is in contact with a buffer circuit B22. The output terminal T2 is in contact with the source electrode 23 of the working electrode 20 via the buffer circuit B21, and is in contact with the drain electrode 24 of the working electrode 20 via a resistance R2 and the buffer circuit B22.

In the source follower pH measuring circuit shown in FIG. 3, the electric charges in the measured liquid W affect the interfacial potential of the gate 16 and the gate 26, thereby, an electric potential is produced at each of the gate 16 of the reference electrode 10 and the gate 26 of the working electrode 20. In the pH measuring circuit shown in FIG. 3, a voltage based on the source electrode 13 and the gate 16 of the reference electrode 10 is produced at the output terminal T1. On the other hand, a voltage based on the source electrode 23 and the gate 26 of the working electrode 20 is produced at the output terminal T2. The difference between the voltage value of the output terminal T1 and the voltage value of the output terminal T2 relates to the pH of the measured liquid W.

Figure 4A:
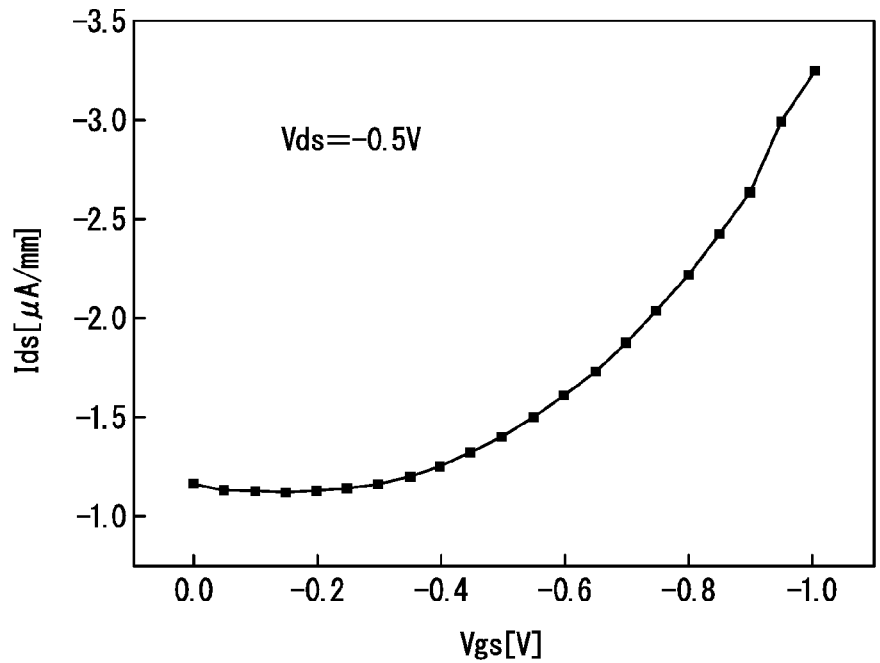
FIG. 4A is a diagram showing an example of property of p-channel field-effect transistor provided in the pH sensor as a sensor device according to the first embodiment of the present invention.
Figure 4B:
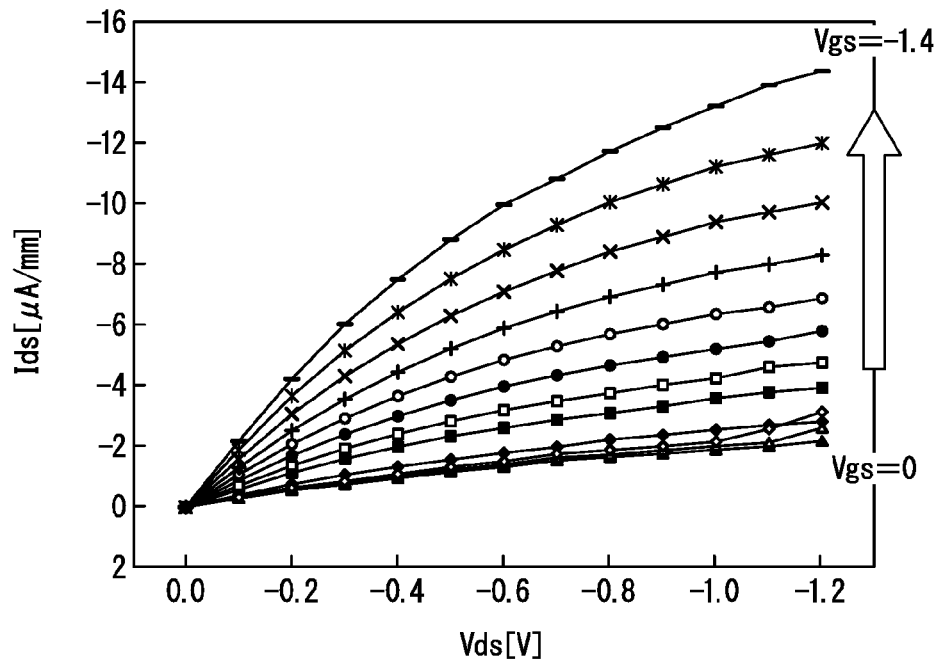
FIG. 4B is a diagram showing an example of property of the p-channel field-effect transistor provided in the pH sensor as a sensor device according to the first embodiment of the present invention.

FIGS. 4A and 4B are diagrams showing an example of property of p-channel field-effect transistor provided in the pH sensor as a sensor device according to the first embodiment of the present invention. The properties shown in FIGS. 4A and 4B are, for example, evaluation results of the property of the source-grounded p-channel field-effect transistor provided in the working electrode 20 of the pH sensor 1. The electric current and voltage magnitude of the p-channel field-effect transistor provided in the reference electrode 10 of the pH sensor 1 are not the same as those of the p-channel field-effect transistor provided in the working electrode 20, but the electric current and voltage magnitude of the p-channel field-effect transistor provided in the reference electrode 10 exhibits almost the same properties as those shown in FIGS. 4A and 4B.

FIG. 4A is a diagram showing the relationship between a voltage (Vgs) of the reference electrode and an electric current (Ids) flowing through the drain electrode and the source electrode when a voltage (Vds) applied between the drain electrode and the source electrode is set to be constant (−0.5 [V]). FIG. 4A shows that the electric current (Ids) flowing through the drain electrode and the source electrode rapidly increases when the voltage (Vgs) of the reference electrode is between approximately −0.4V and approximately −0.5V.

FIG. 4B is a diagram showing the relationship between a voltage (Vds) applied between the drain electrode and the source electrode and an electric current (Ids) flowing through the drain electrode and the source electrode when a voltage (Vgs) of the reference electrode is changed in some range (in the range from 0 to −1.4 [V]). FIG. 4B shows a tendency that a characteristic curve in FIG. 4B is generally shifted upward and the electric current (Ids) flowing through the drain electrode and the source electrode increases as the voltage (Vgs) of the reference electrode increases.

When the pH value of the measured liquid W increases, the characteristic curve in FIG. 4B is shift upward. On the other hand, when the pH value of the measured liquid W decreases, the characteristic curve in FIG. 4B is shift downward. When the pH value of the measured liquid W increases while the electric current (Ids) flowing through the drain electrode and the source electrode is constant, the voltage (Vgs) of the reference electrode decreases. The pH value of the measured liquid W can be obtained from the voltage (Vgs) of the reference electrode using the properties described above.

<Method for Forming Field-Effect Transistor and Method for Treating Diamond Thin Film>

Next, a method for forming the pH sensor 1 will be described below. Hereinafter, in a series of forming processes of the pH sensor 1, only the method for forming the p-channel field-effect transistor provided in the reference electrode 10 and the working electrode 20, and the method for treating the diamond thin film used in the forming method will mainly be described below.

Figure 5A:
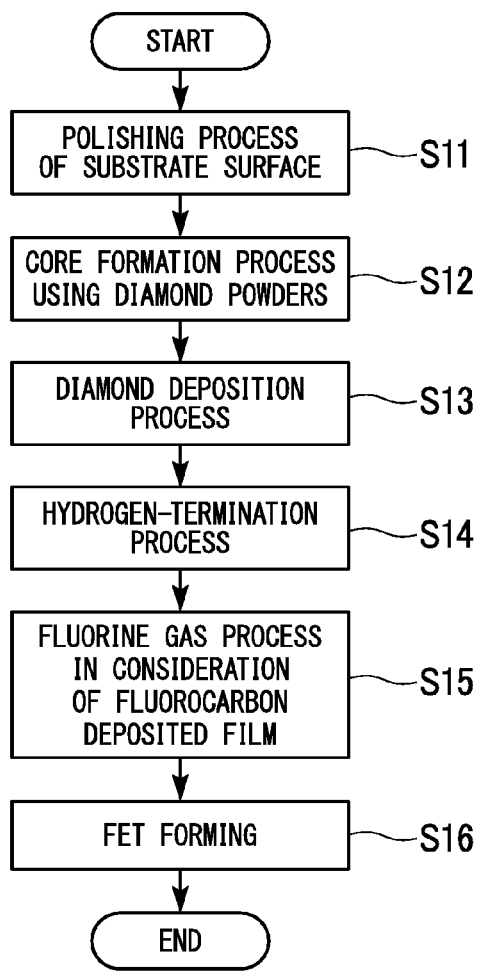
FIG. 5A is a flowchart showing a method for forming a field-effect transistor according to the first embodiment of the present invention.
Figure 5B:
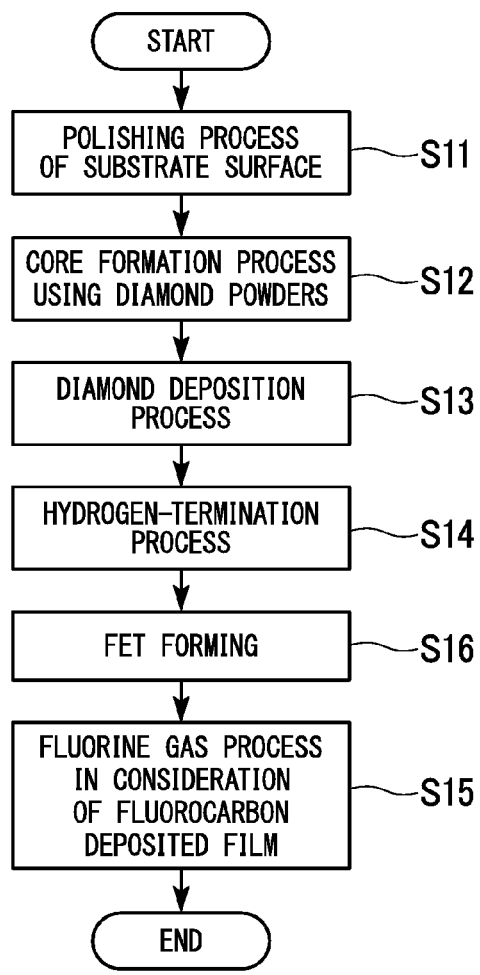
FIG. 5B is a flowchart showing a method for forming the field-effect transistor according to the first embodiment of the present invention.

FIGS. 5A and 5B are flowcharts showing a method for forming a field-effect transistor according to the first embodiment of the present invention. When the forming of the p-channel field-effect transistor starts, as shown in FIG. 5A, a process for polishing the surfaces of silicon wafers 11 and 21 is performed (step S11). Specifically, when the silicon wafers 11 and 21 are polished, in order to improve the adhesion between the silicon wafers 11 and 21 and the diamond thin films 12 and 22, respectively, it is preferable to set that the arithmetic average roughness Ra is from 0.1 to 15 μm and the maximum height Rz is from 1 to 100 μm. The diamond thin films 12 and 22 are formed in a later process.

After the polishing process is completed, a core formation process is performed where a core formation using diamond powders is performed with respect to the surfaces of the polished silicon wafers 11 and 21 (step S12). This process is performed for making the uniform diamond thin films 12 and 22 grow on the surfaces of the silicon wafers 11 and 21. As the method for forming cores using diamond powders, a method for applying a liquid including diamond fine particles on the surfaces of the silicon wafers 11 and 21 using an ultrasonic method, a dipping method, and other methods, and drying the solvent, and the like may be used.

After the core formation using diamond powders is completed, for example, using a hot filament CVD method, the diamond thin films 12 and 22 are deposited on the surfaces of silicon wafers 11 and 21, respectively (step S13: a first step). Specifically, a carbon source (for example, a low molecular organic compound such as methane, alcohol, and acetone) along with a hydrogen gas and the like is provided to the filament. If necessary, a dopant (for example, boron) along with the carbon source, the hydrogen gas, and the like is also provided to the filament. Then, the silicon wafers 11 and 21 are disposed so that the filament is heated to a temperature range at which a carbon radical and the like generate (for example, from 1800 to 2800° C.) and the temperature of the atmosphere is in a temperature range at which a diamond is deposited (for example, from 750 to 950° C.).

The supply rate of the mixed gas including the carbon source, the dopant, the hydrogen gas, and the like is dependent on the size of a reaction container. It is preferable that the pressure is from approximately 2 to approximately 100 [kPa]. A diamond fine particle layer, which generally includes particles having a particle size from 0.001 to 2 μm, is deposited on the silicon wafers 11 and 21. It is possible to control the thickness of the diamond fine particle layer by adjusting the deposition time. In light of the economic efficiency, it is preferable to set to be from 0.5 to 20 μm. If unnecessary, the steps S11 and S12 may be omitted. The step S13 may include a step S14 described below.

After the diamond deposition process is completed, a hydrogen-termination process is performed with respect to the diamond thin films 12 and 22 (as-grown diamond) deposited on the silicon wafers 11 and 21, respectively (step S14: a second process). Specifically, a process for increasing the density of the hydrogen terminal is performed by replacing the terminal (for example, a carbon terminal and an oxygen terminal) of the surface of each deposited diamond thin film 12 and 22, which is not a hydrogen terminal, with a hydrogen terminal. Any one of a process using a hydrofluoric acid solution, a hydrogen plasma process, a heating process in hydrogen atmosphere, a hydrogen radical process, and a cathodic reduction method may be selected as the hydrogen-termination process. The combination of two types of these methods may be used in order to enhance the efficiency of the hydrogen-termination process.

In the hydrogen plasma process, the hydrogen density of the terminal at the surface of each diamond thin film 12 and 22 can be increased under conditions of, for example, 1[kW], $H_2$-flow 400 [sccm], and a plasma irradiation time of five hours. As the cathodic reduction method, for example, a method for applying a voltage of −1.8 [V] to a conductive diamond electrode in an as-grown state and immersing it in 0.1 M sulfuric solution ($H_2SO_4$) for 30 minutes or more may be used.

After the hydrogen termination process is completed, in consideration of the presence and absence of a fluorocarbon deposited film, a fluorine gas process is performed (step S15: a second step). Specifically, based on required surface properties of the diamond thin films 12 and 22, any one of following first and second substitution processes is selected and performed.

First substitution process: a process for substituting part of hydrogen-terminals of each diamond thin film 12 and 22 with fluorine-terminals in the absence of a fluorocarbon deposition on the surface of each diamond thin film 12 and 22

Second substitution process: a process for substituting part of hydrogen-terminals of each diamond thin film 12 and 22 with fluorine-terminals in the presence of the fluorocarbon deposition on the surface of each diamond thin film 12 and The first substitution process is achieved by performing an exposure process using a fluorine gas or a fluorine-based gas with respect to the whole surface or the partial area (the area functioning as the gates 16 and 26) of the surface of each diamond thin film 12 and 22. For example, a fluorine gas ($F_2$ gas) attenuated by a nitrogen gas ($N_2$ gas) is used as a process gas, the process temperature is set to be 20° C., and the process time is set to be approximately 10 hours. Otherwise, the first substitution process is achieved by performing a reactive ion etching (RIE) process or an inductive coupled plasma-RIE (ICP-RIE) using a fluorine-based gas with respect to the area.

On the other hand, the second substitution process is achieved by performing a reactive ion etching (RIE) process or an inductive coupled plasma-RIE (ICP-RIE) using a fluorine-based gas with respect to the whole surface or the partial area (the area functioning as the gates 16 and 26) of the surface of each diamond thin film 12 and 22. For example, when the ICP-RIE process is performed, an octafluoropropane gas ($C_3F_8$ gas) is used as a process gas, the ICP power source output is set to be 500 [W], the bias output is set to be from 0 to 20 [W], the gas pressure is set to be 3 [Pa], the flow rate of $C_3F_8$ gas is set to be 20 [sccm], and the process time is set to be 5 [sec].

The fluorine-based gas described above refers to a collective term of gas including "F" in the molecular formula. The examples of the fluorine-based gas include $C_xF_y$ gas (for example, $CF_4$, $C_2F_6$, $C_3F_8$, and $C_4F_8$), $C_xH_yF_z$ gas (for example, $CHF_3$, $CH_2F_2$, and $CH_3F$), $S_xF_y$ gas (for example, $SF_6$), $N_xF_y$ gas (for example, $NF_3$), $C_xO_yF_z$ gas (for example, $COF_2$), $N_xO_yF_z$ gas (for example, $F_3NO$), $S_xO_yF_z$ gas (for example, SOFA and the like. In addition, the fluorine-based gas includes a mixed gas including the fluorine-based gas described above.

As the fluorine-based gas used for the exposure process in the first substitution process, any of the fluorine-based gas described above may be selected in accordance with the desired effects, for example, $XeF_2$, $COF_2$, and the like may be used. As the fluorine-based gas used for the ICP-RIE process in the first and second substitution processes, any of the fluorine-based gas described above may be selected in accordance with the desired effects, for example, $CF_4$, $C_3F_8$, $C_4F_8$, $CHF_3$, $SF_6$, and the like may be used.

After the fluorine gas process is completed in consideration of the presence and absence of the fluorocarbon deposited film, a process for forming a p-channel field-effect transistor is performed (step S16: a third step). This step is divided into an electrode forming process and a protection film forming process.

In the electrode forming process, first, the surface of each diamond thin film 12 and 22 is spin coated with a resist, and the surface is exposed and developed to pattern the resist. Then, Au or Ti sputtering and liftoff are performed to form an Au or TI thin film, which has the planar view configuration shown in FIG. 2, on the diamond thin films 12 and 22. Thereby, a source electrode 13 and a drain electrode 14 are formed on the diamond thin film 12, and a source electrode 23 and a drain electrode 24 are formed on the diamond thin film 22.

In the protection film forming process, the silicon wafer 11, on which the diamond thin film 12 and the Au or Ti thin film are formed, is spin coated with a resist, which is to be a protection film 15, and the resist is patterned by performing an exposure and development. The silicon wafer 21, on which the diamond thin film 22 and the Au or Ti thin film are formed, are spin coated with a resist, which is to be a protection film 25, the resist is patterned by performing an exposure and development. The diamond thin films 12 and 22 are exposed in the areas where the resists are removed. The area where the diamond thin film 12 is exposed acts as a gate 16, and the area where the diamond thin film 22 is exposed acts as a gate 26.

After the processes described above are performed, the reference electrode 10 and the working electrode 20, each of which the p-channel field-effect transistor is formed in, are obtained. The pH sensor 1 shown in FIG. 1 is obtained by making the reference electrode 10 and the working electrode 20 be opposite to each other so that the source electrodes 13 and 23 are overlapped in planar view and the drain electrodes 14 and 24 are overlapped in planar view, and by separating the reference electrode 10 and the working electrode 20 by a predetermined distance.

The qualitative and quantitative feature of the terminals (fluorine-terminal, oxide-terminal, hydrogen-terminal, and the like) of the diamond surface formed by the above-mentioned processes may be inspected by an analyzing method known in the prior art, for example, X-ray Photoelectron Spectroscopy (XPS), Fourier transform infrared spectrometer (FT-IR). In the flowchart shown in FIG. 5A, the p-channel field-effect transistor is formed (step S16) after the fluorine gas process (step S15) is performed in consideration of the presence and absence of the fluorocarbon deposited film. As the flowchart shown in FIG. 5B, step S16 and step S15 may be reversed.

Figure 6A:
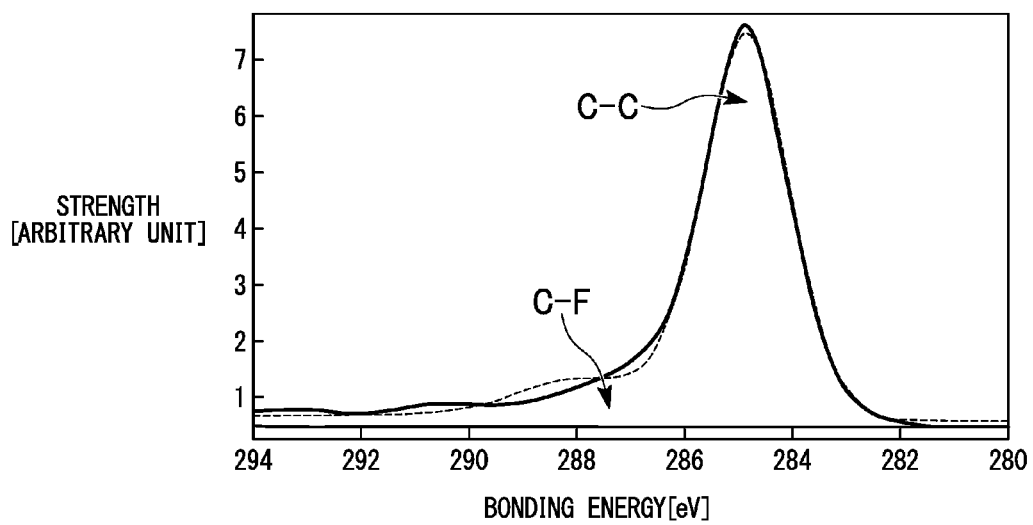
FIG. 6A is a diagram showing analysis results of a diamond thin film treated by a method for treating a diamond thin film according to the first embodiment of the present invention.
Figure 6B:
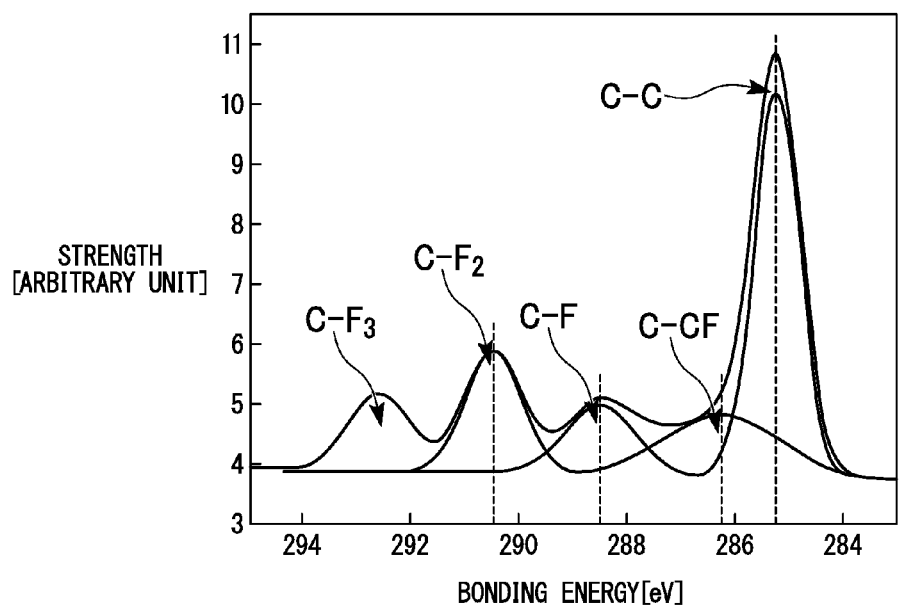
FIG. 6B is a diagram showing analysis results of the diamond thin film treated by the method for treating the diamond thin film according to the first embodiment of the present invention.
Figure 7A:
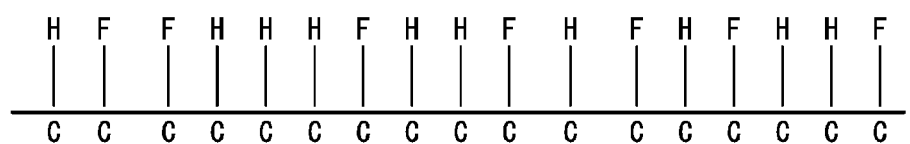
FIG. 7A is a diagram schematically showing surface state of the diamond thin film treated by the method for treating the diamond thin film.
Figure 7B:
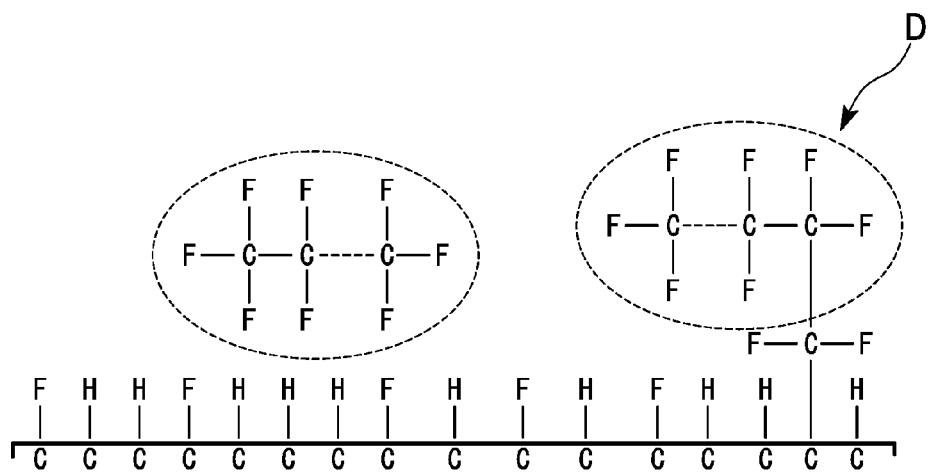
FIG. 7B is a diagram schematically showing surface state of the diamond thin film treated by the method for treating the diamond thin film.

FIGS. 6A and 6B are diagrams showing analysis results of a diamond thin film treated by a method for treating a diamond thin film according to the first embodiment of the present invention. FIGS. 7A and 7B are diagrams schematically showing surface state of the diamond thin film treated by the same treatment method. FIGS. 6A and 7A are diagrams respectively showing analysis results and surface state of the diamond thin film processed by the first substitution process, and FIGS. 6B and 7B are diagrams respectively showing analysis results and surface state of the diamond thin film processed by the second substitution process. FIGS. 6A and 6B show the analysis results using the X-ray Photoelectron Spectroscopy (XPS) described above.

First, FIG. 6A shows a large peak indicating a carbon-carbon bond (C—C) and a small peak indicating a carbon-fluorine bond (C—F), but does not show a peak other than these two peaks. Therefore, as shown in FIG. 7A, a part of the diamond surface processed by the first substitution process is fluorine-terminated, but almost the diamond surface is hydrogen-terminated, and the fluorocarbon deposited film is not formed on the diamond surface (or the fluorocarbon deposition is hardly performed on the diamond surface).

Next, FIG. 6B shows, in addition to a large peak indicating a carbon-carbon bond (C—C) and a small peak indicating a carbon-fluorine bond (C—F), new three peaks indicating a carbon-carbon fluoride bond (C—CF) and carbon-fluorine bonds (C—$F_2$ and C—$F_3$). Therefore, as shown in FIG. 7B, a part of the diamond surface processed by the second substitution process is fluorine-terminated and the fluorocarbon deposited film D is formed on the diamond surface.

As described above, according to the present embodiment, by performing the first substitution process with respect to the diamond thin film, part of the hydrogen-terminals of the diamond thin film can be substituted with the fluorine-terminals in the absence of a fluorocarbon deposition on the surface of the diamond thin film. On the other hand, by performing the second substitution process with respect to the diamond thin film, part of the hydrogen-terminals of the diamond thin film can be substituted with the fluorine-terminals in the presence of the fluorocarbon deposition on the surface of the diamond thin film. Therefore, according to the present embodiment, it is possible to make the diamond surface have desired features.

When the surface of the diamond thin film becomes an ion-sensitive terminal by performing the first substitution process, the first substitution process may be performed during the formation of the p-channel field-effect transistor in the working electrode 20 (specifically, during the treatment of the surface of the diamond thin film 22). When the surface of the diamond thin film becomes an ion-insensitive terminal by performing the second substitution process, the second substitution process may be performed during the formation of the p-channel field-effect transistor in the reference electrode 10 (specifically, during the treatment of the surface of the diamond thin film 12).

In contradiction to the embodiment described above, the surface of the diamond thin film may become an ion-insensitive terminal by performing the first substitution process, and the surface of the diamond thin film may become an ion-sensitive terminal by performing the second substitution process. In this case, the first substitution process may be performed during the formation of the p-channel field-effect transistor in the reference electrode 10, and the second substitution process may be performed during the formation of the p-channel field-effect transistor in the working electrode 20.

As described above, according to the present embodiment, both a field-effect transistor where a fluorocarbon deposited film is not formed on the surface of each diamond thin film 12 and 22, and a field-effect transistor where a fluorocarbon deposited film is formed on the surface of each diamond thin film 12 and 22 can be formed. Thereby, a field-effect transistor having desired ion sensitivity can be easily formed.

In the pH sensor 1 according to the present embodiment, the surface of the diamond thin film 12, which acts as the gate 16 of the p-channel field-effect transistor formed in the reference electrode 10, contacts with the measured liquid W and the surface of the diamond thin film 22, which acts as the gate 26 of the p-channel field-effect transistor formed in the working electrode 20, contacts with the measured liquid W. Therefore, the pH sensor 1 has excellent resistance to high-temperature, high-pressure, acid, and alkaline. Therefore, even under a condition of strong acid or strong alkaline in a semiconductor forming process, or of bioprocess for processing biologically-relevant materials such as protein, the pH value can be measured accurately.

(Second Embodiment)

Figure 8:
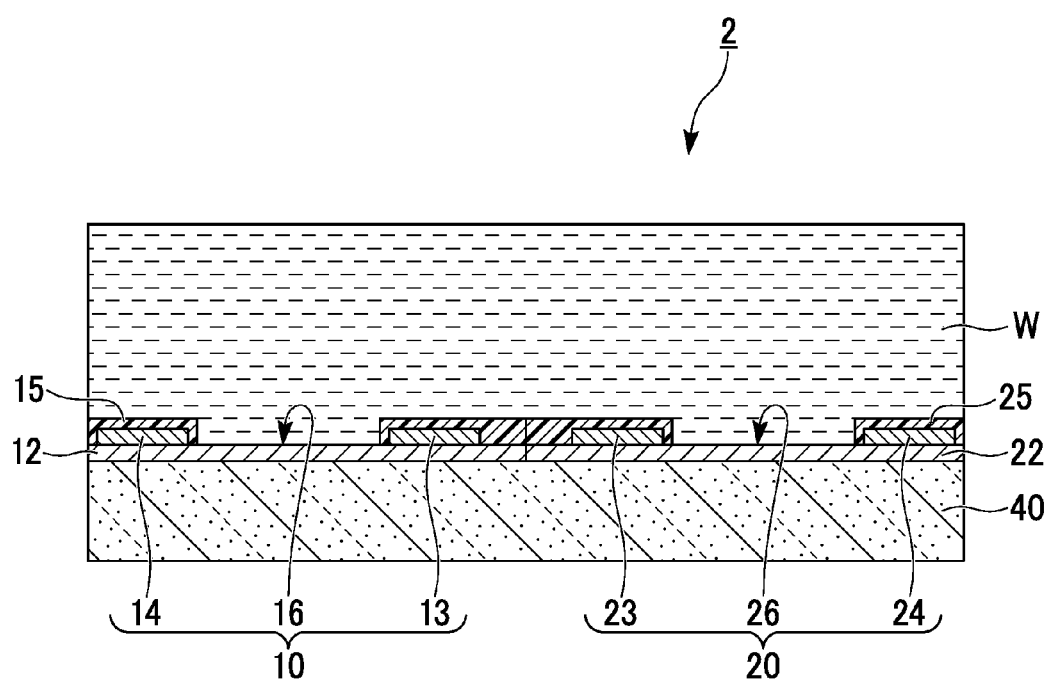
FIG. 8 is a cross-section diagram showing a configuration of a pH sensor as a sensor device according to a second embodiment of the present invention.

FIG. 8 is a cross-section diagram showing a configuration of a pH sensor as a sensor device according to a second embodiment of the present invention. In FIG. 8, elements that are the same as those in FIG. 1 are assigned the same reference numerals. In the pH sensor 1 according to the first embodiment, the reference electrode 10 and the working electrode 20 are formed using the silicon wafer 11 and the silicon wafer 21, which is different from the silicon wafer 11, respectively, the pH of the measured liquid W directed between the reference electrode 10 and the working electrode 20 is measured. On the other hand, in a pH sensor 2 according to the present embodiment, a reference electrode 10 and a working electrode 20 are formed using a common silicon wafer 40 (substrate), the pH of the measured liquid W directed to the silicon wafer 40 (on the reference electrode 10 and the working electrode 20). A conductive material (metal, and the like) is used as a pseudo-reference electrode 30 (not shown).

As shown in FIG. 8, the reference electrode 10 includes a diamond thin film 12, a source electrode 13, a drain electrode 14, and a protection film 15. The diamond thin film 12 is formed on the surface of silicon wafer 40, and the source electrode 13 and the drain electrode 14 are formed on the surface of diamond thin film 12 so as to be parallel to the single substrate. The protection film 15 is formed on the diamond thin film 12 to cover the source electrode 13 and the drain electrode 14. In the reference electrode 10, the area between the source electrode 13 and the drain electrode 14 (the surface of the diamond thin film 12) acts as a gate 16.

Elements of the surface terminal of the diamond thin film 12, which acts as the gate 16, are controlled so that the electrical potential is stable when the hydrogen ion concentration is in the range from $1.0 \times 10^{-1}$ to $1.0 \times 10^{-14}$ mol/L, or the electrical potential is maintained constant without substantially causing problems of ion sensitivity. Namely, in a similar way to the first embodiment, the surface of diamond thin film 12, which acts as the gate 16, is set to be an ion-insensitive terminal.

The working electrode 20 includes a diamond thin film 22, a source electrode 23, a drain electrode 24, and a protection film 25. The diamond thin film 22 is formed on a different area of the surface of silicon wafer 40 than the area on which the reference electrode 10 is formed. The source electrode 23 and the drain electrode 24 are formed on the surface of the diamond thin film 22 so as to be opposite to each other. The protection film 25 is formed on the diamond thin film 22 to cover the source electrode 23 and the drain electrode 24. In the working electrode 20, the area between the source electrode 23 and the drain electrode 24 (the surface of diamond thin film 22) acts as a gate 26. It is preferable to make the source electrode 23 and the drain electrode 24 have the same shape as those of the source electrode 13 and the drain electrode 14 provided in the reference electrode 10, respectively.

Elements of the surface terminal of the diamond thin film 22, which acts as the gate 26, are controlled so that the electrical potential linearly- or non-linearly-changes based on the pH value when the hydrogen ion concentration is in the range from $1.0 \times 10^{-1}$ to $1.0 \times 10^{-14}$ mol/L. Namely, the surface of the diamond thin film 22, which acts as the gate 26, is set to be an ion-sensitive terminal.

The terminal controls of the surface of the diamond thin film 12, which acts as the gate 16, and of the surface of the diamond thin film 22, which acts as the gate 26, can be performed in a similar way to those of the first embodiment. Namely, the terminal controls of the surfaces of the diamond thin film 12 and 22 can be performed by performing the fluorine gas process in consideration of the presence and absence of the fluorocarbon deposited film (refer to step S15 shown in FIGS. 5A and 5B).

When the pH of a measured liquid W is measured by the pH sensor 2 shown in FIG. 8, the measured liquid W is directed to the silicon wafer 40 (on the reference electrode 10 and the working electrode 20). Thereby, in the reference electrode 10, the area between the source electrode 13 and the drain electrode 14 (the surface of the diamond thin film 12), which acts as the gate 16, contacts with the measured liquid W. On the other hand, since the source electrode 13 and the drain electrode 14 are covered with the protection film 15, the source electrode 13 and the drain electrode 14 do not contacts with the measured liquid W.

In the working electrode 20, the area between the source electrode 23 and the drain electrode 24 (the surface of the diamond thin film 22), which acts as the gate 26, contacts with the measured liquid W. On the other hand, since the source electrode 23 and the drain electrode 24 are covered with the protection film 25, the source electrode 23 and the drain electrode 24 do not contacts with the measured liquid W.

As described above, when the pH of the measured liquid W is measured by the pH sensor 2, in a similar way to the pH sensor 1, the area (the surface of the diamond thin film 12), which acts as the gate 16 of the reference electrode 10, contacts with the measured liquid W, and the area (the surface of the diamond thin film 22), which acts as the gate 26 of the working electrode 20, contacts with the measured liquid W. Therefore, the pH of the measured liquid W is measured by a similar principle to that of the pH sensor 1 according to the first embodiment.

Hereinbefore, the method for treating the surface of diamond thin film, the method for forming the field-effect transistor, and the sensor device according to the embodiments of the present invention were described. The present invention is not limited to the embodiments, and may be freely changed within the scope of the present invention. For example, the embodiment that the surfaces of the diamond thin films 12 and 22 formed on the silicon wafers 11, 21, and 40 are processed was described. However, the diamond thin film to be processed is not necessary to be formed on the substrate (a silicon substrate or a carbon substrate), the substrate may be omitted (a diamond bulk body may be used). The diamond thin film may have a polycrystalline structure or a monocrystalline structure.

Figure 9A:
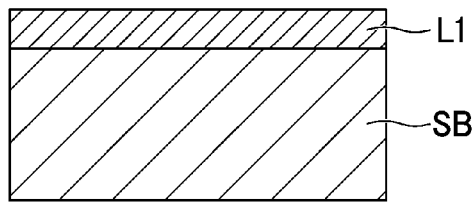
FIG. 9A is a diagram showing an example of a diamond substrate which is applicable to embodiments of the present invention.
Figure 9B:
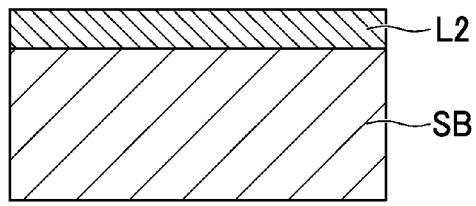
FIG. 9B is a diagram showing an example of a diamond substrate which is applicable to the embodiments of the present invention.

FIGS. 9A to 9H are diagrams showing examples of diamond substrates which are applicable to embodiments of the present invention. In FIGS. 9A to 9H, the silicon wafers 11 and 21 in FIG. 1, or the silicon wafer 40 in FIG. 8 are shown as a substrate SB. A diamond substrate shown in FIG. 9A is that a diamond thin film (a non-doped diamond thin film L1), to which impurities are not added, is formed on the substrate SB, and a diamond substrate shown in FIG. 9B is that a diamond thin film (a doped diamond thin film L2), to which impurities are added, is formed on the substrate SB.

Figure 9C:
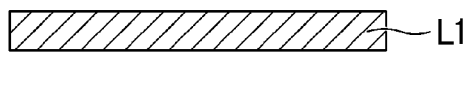
FIG. 9C is a diagram showing an example of a diamond substrate which is applicable to the embodiments of the present invention.
Figure 9D:
FIG. 9D is a diagram showing an example of a diamond substrate which is applicable to the embodiments of the present invention.

A diamond substrate shown in FIG. 9C includes only the non-doped diamond thin film L1 without the substrate SB, and a diamond substrate shown in FIG. 9D is that the doped diamond thin film L2 is formed on the non-doped diamond thin film L1 without the substrate SB. Since the diamond substrates shown in FIGS. 9C and 9D do not include the substrate SB, the diamond substrates shown in FIGS. 9C and 9D may be referred as a free-standing diamond.

Figure 9E:
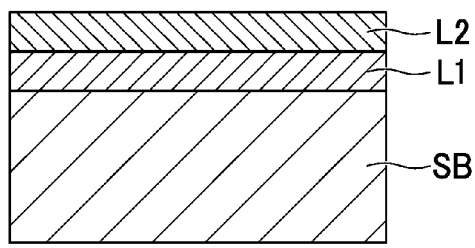
FIG. 9E is a diagram showing an example of a diamond substrate which is applicable to the embodiments of the present invention.

A diamond substrate shown in FIG. 9E is that the doped diamond thin film L2 is formed on the diamond substrate shown in FIG. 9A. If the substrate is used for a sensor device such as the pH sensor 1, the synergetic effect between the semiconductor property of the doped diamond thin film L2 and the insulator property of the non-doped diamond thin film L1 can be expected.

Figure 9F:
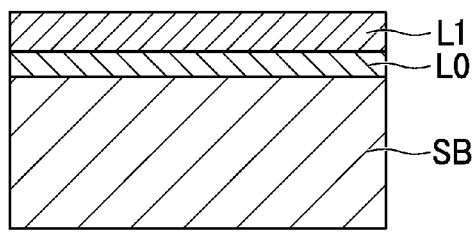
FIG. 9F is a diagram showing an example of a diamond substrate which is applicable to the embodiments of the present invention.
Figure 9G:
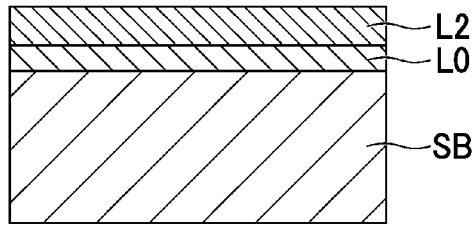
FIG. 9G is a diagram showing an example of a diamond substrate which is applicable to the embodiments of the present invention.
Figure 9H:
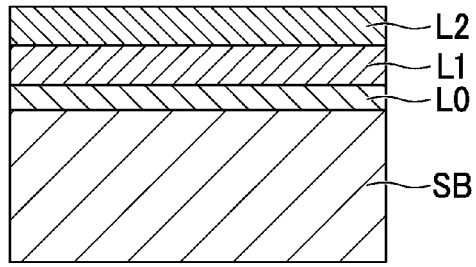
FIG. 9H is a diagram showing an example of a diamond substrate which is applicable to the embodiments of the present invention.

Each diamond substrate shown in FIGS. 9F, 9G, and 9H is that a silicon oxide film ($SiO_2$) L0 is formed on the substrate SB of the diamond substrates shown in FIGS. 9A, 9B, and 9E and at least one of the non-doped diamond thin film L1 and the doped diamond thin film L2 is formed on the silicon oxide film L0. If the substrate is used for a sensor device such as the pH sensor 1, the insulation effect of the silicon oxide film can be expected.

The embodiment that the pseudo-reference electrode as a reference of the reference electrode 10 is the same as that of the working electrode 20 was described above, but the pseudo-reference electrode as a reference of the reference electrode 10 and that of the working electrode 20 may be separately provided. The embodiment that the silicon wafer is used as a substrate was described above, but the material of the substrate is arbitrary. The embodiment that the hydrogen-termination process is performed before performing the first and second substitution processes was described above, but, if the required surface property of the diamond thin film can be obtained without the hydrogen-termination process, the hydrogen-termination process may be omitted.

The method for forming the diamond thin film on the substrate is not limited to the method described above, and arbitrary methods may be used. A vapor phase synthesis method may be used as a representative forming method, and the vapor phase synthesis method includes a CVD (Chemical Vapor Deposition) method, a Physical Vapor Deposition (PVD) method, a plasma jet method, and the like. The CVD method includes a Hot Filament CVD method, a Microwave Plasma CVD method, and the like.

Whatever diamond deposition method is used, there are some cases where the synthesized diamond thin film has a polycrystalline structure, and an amorphous carbon or a graphite composition is present in the diamond thin film. It is preferable that the amorphous carbon and the graphite composition are less in terms of the stability of the diamond thin film. In a Raman spectroscopic analysis, it is preferable that the ratio between a peak strength l(D) assigned to a diamond, which is present near 1332 $cm^{-1}$ (the range from 1321 to 1352 $cm^{-1}$), and a peak strength I(G) assigned to G band of a graphite, which is present near 1580 $cm^{-1}$ (the range from 1560 to 1600 $cm^{-1}$), namely, I(D)/I(G) is equal to or greater than 1, and the content of the diamond is greater than that of the graphite.

The embodiment that a sensor device is a pH sensor was described above, the present invention is also applicable to sensor devices other than a pH sensor (for example, biosensor). Some biosensors include only one detection electrode corresponding to the reference electrode 10 or the working electrode 20, but the present invention is also applicable to such the biosensor.

The embodiment that field-effect transistors having different ion-sensitivities are formed by performing the first and second substitution processes in step S15 shown in FIG. 5 was described above. It is possible to form field-effect transistors having different chemical absorption properties. Namely, according to the present invention, it is possible to form field-effect transistors adapted to various purposes.

EXAMPLES

The inventors of the present application actually treated a surface of a diamond thin film using the method for treating the surface of the diamond thin film described above, and actually formed a field-effect transistor using the method for forming the field-effect transistor described above. The properties of the processed diamond thin film were measured, and the properties of the formed field-effect transistor were measured. Hereinafter, first to third examples that the first substitution process with respect to a surface of a diamond thin film is performed to form a field-effect transistor, and a fourth example that the second substitution process with respect to a surface of a diamond thin film is performed will be described.

First Example

Figure 10:
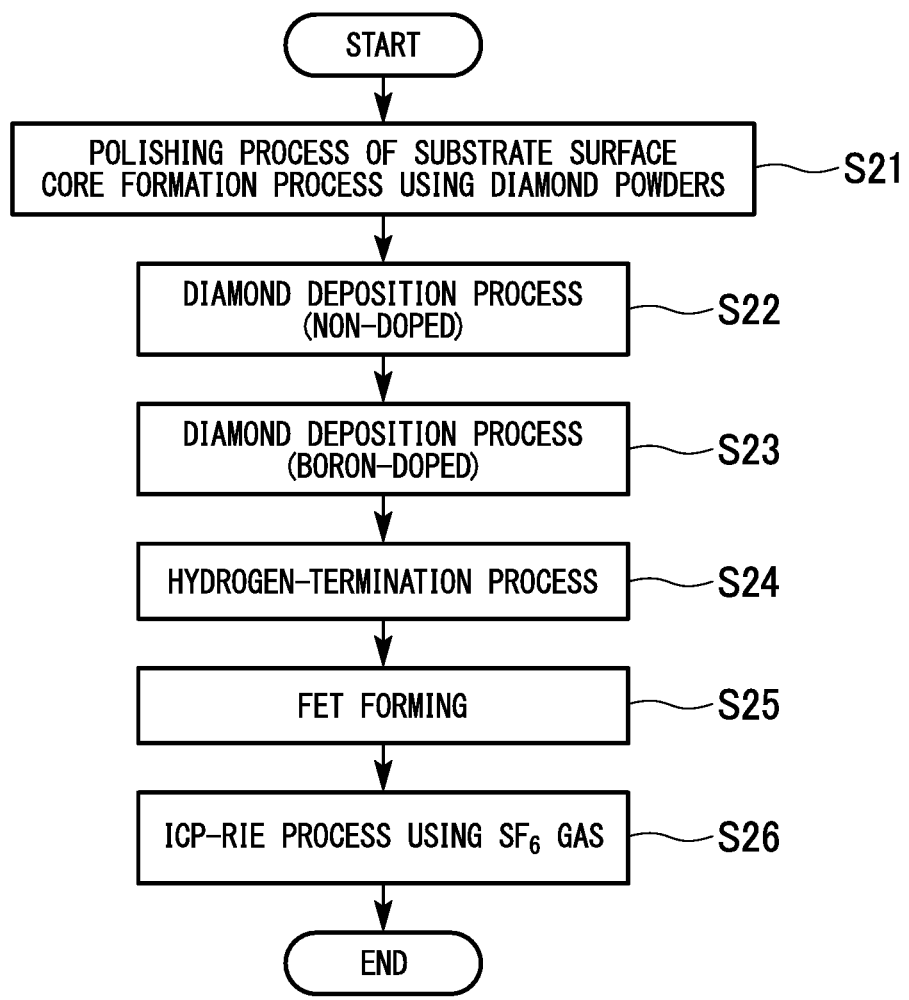
FIG. 10 is a flowchart showing a method for forming a field-effect transistor according to a first example.

In the present example, a substitution process of part of hydrogen-terminals of a diamond thin film with fluorine-terminals by performing an ICP-RIE process using $SF_6$ gas, in the absence of a fluorocarbon deposition, is performed to form a field-effect transistor. FIG. 10 is a flowchart showing a method for forming a field-effect transistor according to the first example.

As shown in FIG. 10, in the present example, a polishing process of a surface of a silicon wafer, and then, a core formation process using diamond powders with respect to the surface of the polished silicon wafer, were performed (step S21). Next, a non-doped diamond thin film was deposited on the surface of the silicon wafer, on which the core formation process was performed, using a hot filament CVD method (step S22), and a boron-doped diamond thin film was deposited on the non-doped diamond thin film using a Microwave Plasma CVD method (step S23). The deposition conditions that, for example, the methane concentration is set to be from 0.01 to 1%, the B/C ratio is set to be from 1000 to 15000 ppm, and the deposition time is set to be from 1 to 10 minutes, were used.

Next, a hydrogen-termination process was performed using a Microwave Plasma CVD method (step S24), and then, a field-effect transistor was formed (step S25). Finally, an ICP-RIE process using $SF_6$ gas was performed with respect to the surface of the diamond thin film, which acts as a gate (step S26). By the processes described above, the field-effect transistor including the fluorine-terminated gate was obtained. The ICP-RIE process conditions that, for example, the ICP power source output is set to be from 10 to 1000 [W], the vacuum is set to be from approximately 1.33 to approximately 13.3 [Pa], and the process time is set to be from 2 to 3 minutes, were used.

Figure 11:
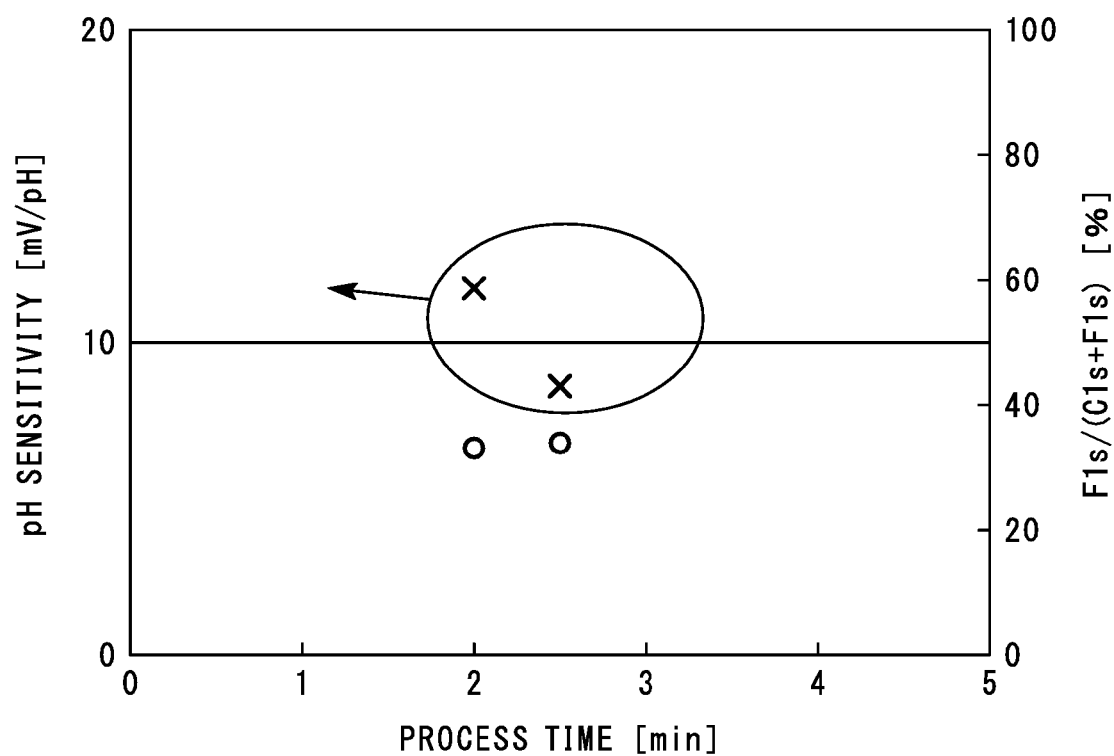
FIG. 11 is a diagram showing an example of property of the field-effect transistor obtained in the first example.

FIG. 11 is a diagram showing an example of property of the field-effect transistor obtained in the first example. In FIG. 11, the properties of the field-effect transistor include the pH sensitivity and the analysis results of X-ray Photoelectron Spectroscopy (XPS). As shown in FIG. 11, the pH sensitivity of the field-effect transistor obtained in the present example was from approximately 8 to approximately 11 [mV/pH]. The analysis results of XPS (F1s/(C1s+F1s)) was from approximately 30 to approximately 60 [%]. FIG. 11 shows only the case that the analysis result of XPS was 30%. Thereby, in the field-effect transistor obtained in the present example, the fact that the surface of the diamond thin film, which acts as the gate, was fluorine-terminated at a predetermined rate, was confirmed.

Second Example

Figure 12:
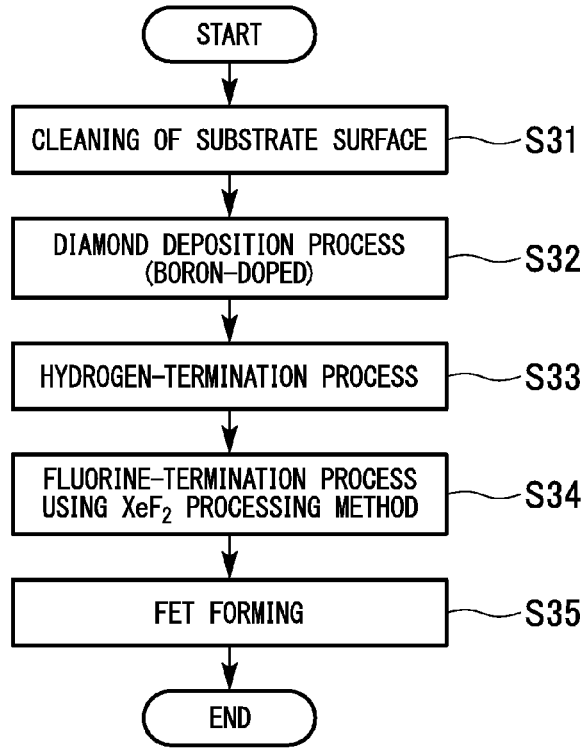
FIG. 12 is a flowchart showing a method for forming a field-effect transistor according to a second example.

In the present example, a substitution process of part of hydrogen terminals of a free-standing diamond (refer to FIG. 9D) with fluorine terminals by performing an exposure process using xenon fluoride ($XeF_2$), in the absence of a fluorocarbon deposition, was performed to form a field-effect transistor. FIG. 12 is a flowchart showing a method for forming a field-effect transistor according to the second example.

As shown in FIG. 12, in the present example, first, a cleaning process of a surface of a polycrystalline diamond substrate (an acid cleaning or an organic solvent cleaning) was performed (step S31). Next, a boron-doped diamond thin film was deposited on the surface of the cleaned polycrystalline diamond substrate using a Microwave Plasma CVD method (step S32). The deposition conditions that, for example, the methane ($CH_4$) concentration is set to be from 0.01 to 1%, the B/C ratio is set to be from 1000 to 15000 ppm, and the deposition time is set to be from 1 to 10 minutes, were used.

Next, a hydrogen-termination process was performed using a Microwave Plasma CVD method (step S33), and then, the solid XeF$_2$ was sublimated to perform an exposure process and to substitute part of hydrogen terminals at the specific area of the boron-doped diamond thin film (the area to be a gate) with fluorine terminals (step S34). The conditions of the exposure process using XeF$_2$ that, for example, the vacuum is set to be approximately 133 [Pa], and the process time is set to be 5 minutes, were used. Finally, a field-effect transistor was formed so that the specific area becomes a gate (step S35). By the processes described above, the field-effect transistor including the fluorine-terminated gate was obtained.

Figure 13:
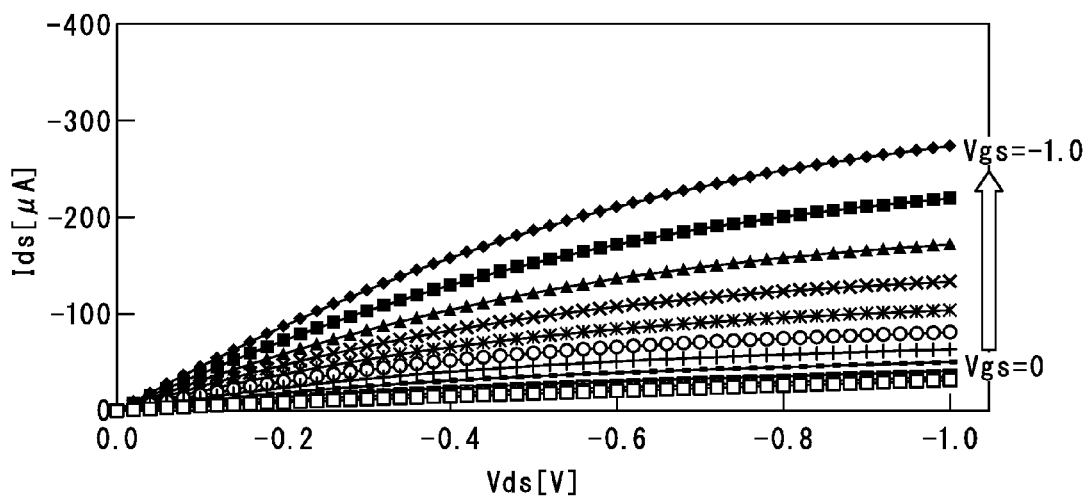
FIG. 13 is a diagram showing an example of electrical current and voltage property of the field-effect transistor obtained in the second example.

FIG. 13 is a diagram showing an example of electrical current and voltage property of the field-effect transistor obtained in the second example. FIG. 13 shows the electrical current and voltage property of the field-effect transistor, which includes a source electrode and a drain electrode, which are made of gold (Au), and has the gate length of 500 [μm] and the gate width of 10 [mm] (the relationship of the electrical current (Ids) flowing through the drain electrode and the source electrode to the voltage (Vds) applied between the drain electrode and the source electrode when the voltage (Vgs) between the gate electrode and the source electrode is changed).

In a similar way to FIG. 4B, FIG. 13 shows a tendency that a characteristic curve in FIG. 13 is generally shifted upward and the electric current (Ids) flowing through the drain electrode and the source electrode increases as the voltage (Vgs) increases. Thereby, it was confirmed that the device according to the present example act as a field-effect transistor. The pH sensitivity of the field-effect transistor obtained in the present example was from approximately 5 to approximately 12 [mV/pH], and the analysis results of XPS (F1s/(C1s+F1s)) was approximately 5 [%]. The pH sensitivity and the analysis results of XPS were omitted from the drawings.

Third Example

Figure 14:
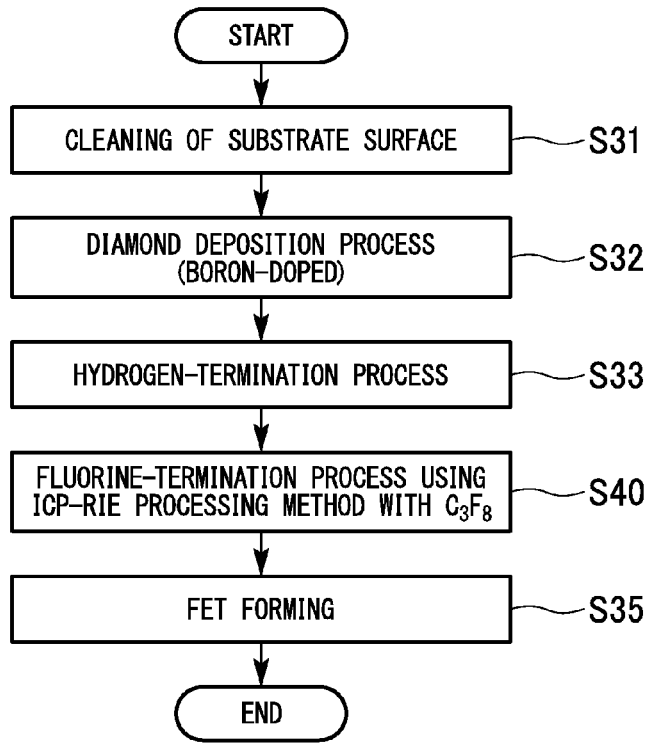
FIG. 14 is a flowchart showing a method for forming a field-effect transistor according to a third example.

In the present example, a substitution process of part of hydrogen terminals of a free-standing diamond (refer to FIG. 9D) with fluorine terminals by performing an ICP-RIE process using C$_3$F$_8$ gas, in the absence of a fluorocarbon deposition, was performed to form a field-effect transistor. FIG. 14 is a flowchart showing a method for forming a field-effect transistor according to the third example.

As shown in FIG. 14, in the present example, in a similar way to the second example, a cleaning process of a surface of a polycrystalline diamond substrate (an acid cleaning or an organic solvent cleaning) (step S31), a deposition process of a boron-doped diamond thin film on the surface of the cleaned polycrystalline diamond substrate using a Microwave Plasma CVD method (step S32), and a hydrogen-termination process using a Microwave Plasma CVD method (step S33) were performed in this order. The deposition conditions in step S32 was set to be the same as those of the second example.

Then, the ICP-RIE process using C$_3$F$_8$ gas was performed to substitute part of hydrogen terminals at the specific area of the boron-doped diamond thin film (the area to be a gate) with fluorine terminals (step S40). The conditions of the ICP-RIE process that the ICP power source output is set to be 100 [W], and the process time is set to be 30 seconds, were used. Finally, a field-effect transistor was formed so that the specific area becomes a gate (step S35). By the processes described above, the field-effect transistor including the fluorine-terminated gate was obtained.

Figure 15:
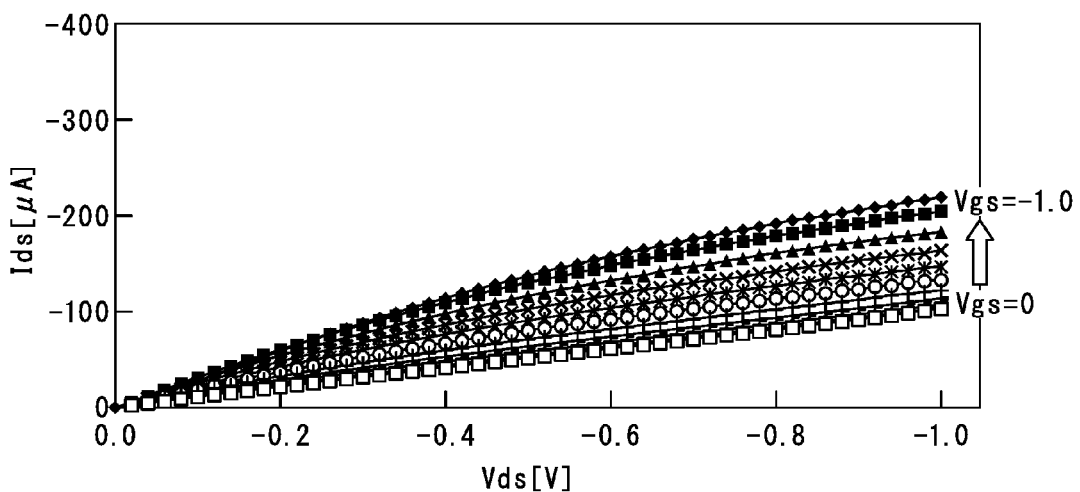
FIG. 15 is a diagram showing an example of electrical current and voltage property of the field-effect transistor obtained in the third example.

FIG. 15 is a diagram showing an example of electrical current and voltage property of the field-effect transistor obtained in the third example. In a similar way to FIG. 13, FIG. 15 shows the electrical current and voltage property of the field-effect transistor, which includes a source electrode and a drain electrode, which are made of gold (Au), and has the gate length of 500 [μm] and the gate width of 10 [mm]. Referring to FIG. 15, the variation width (shift-up width) of the characteristic curve during the change of the voltage (Vgs) was smaller than that of FIG. 13. However, since FIG. 15 shows the similar electrical current and voltage property to that of FIG. 13, it was confirmed that the device according to the present example act as a field-effect transistor.

Figure 16:
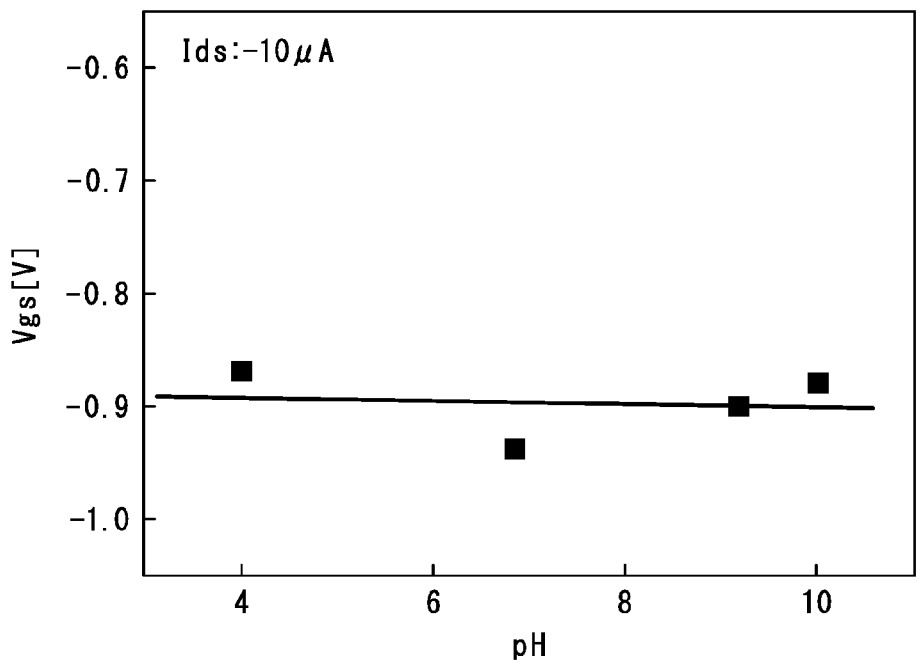
FIG. 16 is a diagram showing an example of pH sensitivity of the field-effect transistor obtained in the third example.

FIG. 16 is a diagram showing an example of pH sensitivity of the field-effect transistor obtained in the third example. In FIG. 16, the horizontal axis indicates a pH value, and the vertical axis indicates a voltage (Vgs) applied between a gate electrode and a source electrode. FIG. 16 shows a tendency that the voltage (Vgs) slightly decreases as the pH increases. Thus, the pH sensitivity of the field-effect transistor obtained in the present example was approximately −1 [mV/pH].

The analysis results (F1s/(C1s+F1s)) of XPS of the field-effect transistor obtained in the present example was approximately 30 [%]. The analysis results were omitted from the drawings. When only the process time of the ICP-RIE process was changed from 30 seconds to 1 minute (other process conditions remained unchanged), the analysis results (F1s/(C1s+F1s)) of XPS was approximately 20 [%]. In the analysis results of XPS of the present example, since a peak indicating a carbon-fluorine bond (C—F$_3$) was not present near C1s peak (the bonding energy is in the range from 280 to 295 [eV]), it was confirmed that the fluorocarbon deposited film was not present.

Fourth Example

Figure 17:
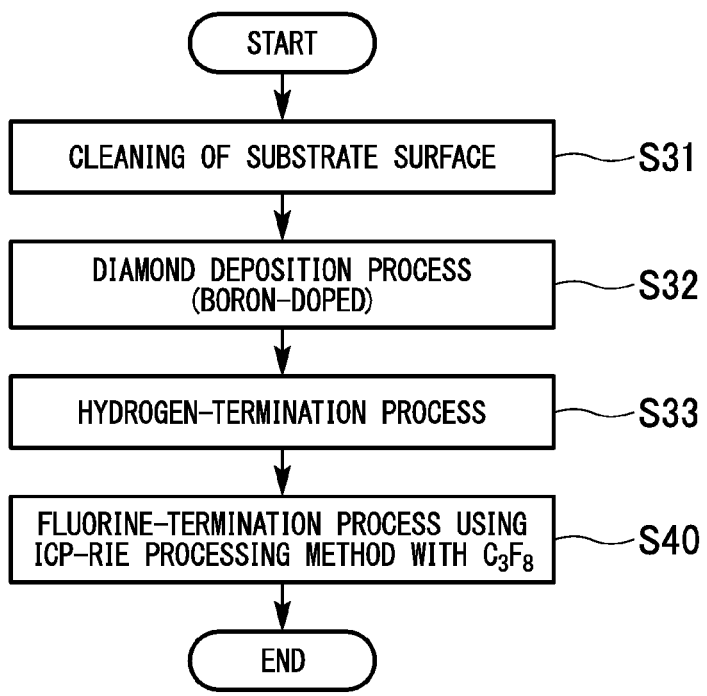
FIG. 17 is a flowchart showing a method for treating a surface of diamond thin film according to a fourth example.

In the present example, a substitution process of part of hydrogen terminals of a diamond thin film with fluorine terminals by performing an ICP-RIE process using C$_3$F$_8$ gas in the presence of a fluorocarbon deposition, was performed. FIG. 17 is a flowchart showing a method for treating a surface of diamond thin film according to the fourth example. As can be seen from the comparison between FIG. 17 and FIG. 14, in the present example, the surface of the diamond thin film is treated in a similar process to that of the third example.

As shown in FIG. 17, in the present example, in a similar way to the third example, a cleaning process of a surface of a polycrystalline diamond substrate (an acid cleaning or an organic solvent cleaning) (step S31), a deposition process of a boron-doped diamond thin film on the surface of the cleaned polycrystalline diamond substrate using a Microwave Plasma CVD method (step S32), and a hydrogen-termination process using a Microwave Plasma CVD method (step S33) were performed in this order. The deposition conditions in step S32 were set to be the same as those of the third example.

Then, the ICP-RIE process using C$_3$F$_8$ gas was performed to substitute part of hydrogen terminals at the specific area of the boron-doped diamond thin film (the area to be a gate) with fluorine terminals (step S40). The conditions of the ICP-RIE process that the ICP power source output is set to be from approximately 300 to approximately 500 [W], and the process time is set to be 30 seconds, were used.

The analysis results (F1s/(C1s+F1s)) of XPS of the field-effect transistor obtained in the present example were approximately 58 [%] when the ICP power source output was set to be 300 [W] and approximately 62 [%] when the ICP power source output was set to be 500 [W]. The analysis results were omitted from the drawings. In the analysis results of XPS of the present example, since a peak indicating a carbon-fluorine bond (C—F$_3$) was present near C1s peak (the bonding energy is in the range from 280 to 295 [eV]), it was confirmed that the fluorocarbon deposited film was formed.

As described above, when an ICP-RIE process using $C_3F_8$ gas is performed, both a diamond thin film where a fluorocarbon deposited film is formed and a diamond thin film where a fluorocarbon deposited film is not formed can be obtained by only changing process conditions of the ICP-RIE process. When step S35 shown in FIG. 14 is performed after step S40 shown in FIG. 17, in a similar way to the third example, a field-effect transistor including a fluorine-terminated gate can be obtained.

In the third and fourth examples, the deposition process of the boron-doped diamond thin film (step S32), the hydrogen-termination process (step S33), the substitution process of part of the hydrogen terminals with the fluorine terminals (step S40), and the forming process of the field-effect transistor (step S35) were performed in this order. However, the forming process of the field-effect transistor (step S35) may be performed after the deposition process of the boron-doped diamond thin film (step S32) and before the hydrogen-termination process (step S33), or after the hydrogen-termination process (step S33) and before the substitution process of part of the hydrogen terminals with the fluorine terminals (step S40).

What is claimed is:

1. A method for forming a transistor, comprising:
   forming a diamond thin film;
   exposing at least a part of a surface of the diamond thin film to a fluorine gas or a fluorine-based gas without carbon to substitute part of hydrogen-terminals of the diamond thin film with fluorine-terminals in the absence of a deposition process of a fluorocarbon deposition film on the surface of the diamond thin film; and
   forming a gate on the part of the surface of the diamond thin film.

2. The method for forming the transistor according to claim 1, wherein the fluorine-based gas used for exposure includes $XeF_2$.

3. The method for forming the transistor according to claim 1, further comprising:
   forming a source electrode and a drain electrode on the diamond thin film after forming the diamond thin film and before performing the substitution process of the hydrogen-terminals of the diamond thin film with fluorine-terminal.

4. The method for forming the transistor according to claim 3, wherein forming the source electrode and the drain electrode comprises forming a protection film for protecting the source electrode and the drain electrode to cover the source electrode and the drain electrode.

5. The method for forming the transistor according to claim 1, further comprising:
   substituting any terminals other than hydrogen-terminals of the surface of the diamond thin film with hydrogen-terminals, prior to performing the substitution process of the hydrogen-terminals of the diamond thin film with fluorine-terminals.

6. A sensor device comprising at least one detection electrode configured to contact with a liquid including a specific material, the sensor device being for detecting the specific material included in the liquid based on output from the detection electrode,
   wherein a transistor formed by a method for forming a transistor according to claim 1 is provided in the detection electrode so as to bring the surface of the diamond thin film acting as the gate with the liquid.

7. A method for forming a transistor, comprising:
   forming a diamond thin film;
   performing an inductive coupled reactive ion etching exposing at least a part of a surface of the diamond thin film to a fluoride-based gas without carbon to substitute part of hydrogen-terminals of the diamond thin film with fluoride-terminals in the absence of a deposition process of a fluorocarbon deposition film on the surface of the diamond thin film; and
   forming a gate on the part of the surface of the diamond thin film.

8. The method for forming the transistor according to claim 7, further comprising:
   substituting any terminals other than hydrogen-terminals of the surface of the diamond thin film with hydrogen-terminals, prior to performing the substitution process of the hydrogen-terminals of the diamond thin film with fluorine-terminals.

9. The method for forming the transistor according to claim 7, wherein the fluorine-based gas used for the inductive coupled reactive ion etching includes at least one of $S_xF_y$, $N_xF_y$, $N_xO_yF_z$, and $S_xO_yF_z$, where each x, y, and z is an integer equal to or greater than 1.

10. A method for forming the transistor, comprising:
    forming a diamond thin film
    doping a surface of the diamond thin film with boron;
    performing an inductive coupled reactive ion etching exposing at least a part of the surface of the boron-doped diamond thin film to a fluorine-based gas with carbon to substitute part of hydrogen-terminals of the diamond thin film with fluorine-terminals in the absence of a deposition process of a fluorocarbon deposition film on the surface of the diamond thin film; and
    forming a gate on the part of the surface of the diamond thin film.

11. The method for forming the transistor according to claim 10, further comprising:
    substituting any terminals other than hydrogen-terminals of the surface of the diamond thin film with hydrogen-terminals, prior to performing the substitution process of the hydrogen-terminals of the diamond thin film with fluorine-terminals.

12. The method for forming the transistor according to claim 10, wherein the fluorine-based gas used for the inductive coupled reactive ion etching includes at least one of $C_xF_y$, $C_xH_yF_z$, and $C_xO_yF_z$, where each x, y, and z is an integer equal to or greater than 1.

13. A method for forming the transistor, comprising:
    forming a diamond thin film
    performing a substitution process for substituting part of hydrogen-terminals of the diamond thin film with fluorine-terminals using a fluorine-based gas with carbon in the presence of a deposition process of a fluorocarbon deposition film on the surface of the diamond thin film, the surface of the diamond thin film having a crystalline structure, the fluorocarbon deposition film having a structure different from the crystalline structure of the surface of the diamond thin film; and
    forming a gate on a part of the surface of the diamond thin film.

14. The method for forming the transistor according to claim 13, further comprising:
    substituting any terminals other than hydrogen-terminals of the surface of the diamond thin film with hydrogen-terminals, prior to performing the substitution process of the hydrogen-terminals of the diamond thin film with fluorine-terminals.

15. The method for forming the transistor according to claim 13, wherein the substitution process is to perform a reactive ion etching exposing at least a part of the surface of the diamond thin film to a fluorine-based gas.

16. The method for forming the transistor according to claim 15, wherein the reactive ion etching is an inductive coupled reactive ion etching.

17. The method for forming the transistor according to claim 15, wherein the fluorine-based gas used for the reactive ion etching includes at least one of $C_xF_y$, $C_xH_yF_z$, and $C_xO_yF_z$, where each x, y, and z is an integer equal to or greater than 1.

* * * * *